United States Patent
Hammer (10) Patent No.: US 9,295,501 B2
(45) Date of Patent: Mar. 29, 2016

(54) BAYONET COUNTER-TORQUE WRENCH

(75) Inventor: Michael Anthony Hammer, Pine Brook, NJ (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 0 days.

(21) Appl. No.: 13/196,635

(22) Filed: Aug. 2, 2011

(65) Prior Publication Data

US 2013/0035729 A1 Feb. 7, 2013

(51) Int. Cl.
*A61B 17/88* (2006.01)
*A61B 17/70* (2006.01)

(52) U.S. Cl.
CPC ......... *A61B 17/7091* (2013.01); *A61B 17/7083* (2013.01)

(58) Field of Classification Search
USPC ......... 606/86 A, 914–916, 104, 99; 81/176.2, 81/176.1
See application file for complete search history.

(56) References Cited

U.S. PATENT DOCUMENTS

| | | | | |
|---|---|---|---|---|
| 920,188 | A * | 5/1909 | Schumacher | 403/190 |
| 2,337,402 | A * | 12/1943 | Mills | B23B 31/113 279/83 |
| 2,411,245 | A * | 11/1946 | Buechler | B25B 13/48 411/350 |
| 2,987,080 | A * | 6/1961 | Chandler et al. | 137/798 |
| 3,477,486 | A | 11/1969 | Modrey | |
| 5,505,732 | A * | 4/1996 | Michelson | 606/86 A |
| 5,797,911 | A | 8/1998 | Sherman et al. | |
| 7,749,258 | B2 | 7/2010 | Biedermann et al. | |
| 7,922,725 | B2 * | 4/2011 | Darst Rice et al. | 606/86 A |
| 8,066,745 | B2 * | 11/2011 | Kirschman | 606/269 |
| 8,142,436 | B2 * | 3/2012 | Kirschman | 606/86 A |
| 8,419,778 | B2 | 4/2013 | Barry | |
| 8,430,914 | B2 | 4/2013 | Spratt et al. | |
| 8,845,651 | B2 * | 9/2014 | Buttler | A61B 17/92 606/86 R |

(Continued)

FOREIGN PATENT DOCUMENTS

| | | | | |
|---|---|---|---|---|
| FR | 2954689 | * | 7/2011 | A61B 17/88 |
| WO | 2011/133160 A1 | | 10/2011 | |

OTHER PUBLICATIONS

International Search Report and Written Opinion, PCT/US2012/049180, dated Oct. 26, 2012, 9 pages.

(Continued)

*Primary Examiner* — Jan Christopher Merene
(74) *Attorney, Agent, or Firm* — Baker & McKenzie LLP (57) ABSTRACT

A counter-torque wrench for use with spinal implantation systems is provided wherein the counter-torque wrench engages a spinal implant rod and a bone screw body in a manner to promote a perpendicular alignment between the longitudinal axis of the rod and the longitudinal axis of the bone screw body, and a co-linear alignment between the longitudinal axis of the bone screw body and the longitudinal axis of the wrench body. The counter-torque wrench may comprise a handle attached to a first end of the counter-torque wrench body and a rod engaging member attached to a second end of the counter-torque wrench body. The rod engaging member may comprise generally opposing slots, wherein each slot comprises a prong extending into each slot, the prong creating a generally L-shaped slot, and a pocket formed by a curved feature of each slot. The opposing slots may be sized and shaped to releasably attach to the spinal implant rod in an engaged position perpendicular to the counter-torque wrench body when the counter-torque wrench is rotated in a counter-clockwise direction.

6 Claims, 5 Drawing Sheets

(56) References Cited

U.S. PATENT DOCUMENTS

| | | | |
|---|---|---|---|
| 2002/0120275 A1 | 8/2002 | Schmieding et al. | |
| 2003/0105460 A1 | 6/2003 | Crandall et al. | |
| 2003/0231927 A1* | 12/2003 | Hale | 403/349 |
| 2004/0176766 A1 | 9/2004 | Shluzas | |
| 2004/0186483 A1* | 9/2004 | Bagby | 606/99 |
| 2004/0225289 A1 | 11/2004 | Biedermann et al. | |
| 2005/0043735 A1 | 2/2005 | Ahmad | |
| 2006/0142762 A1* | 6/2006 | Michelson | 606/61 |
| 2006/0200131 A1 | 9/2006 | Chao et al. | |
| 2007/0043357 A1* | 2/2007 | Kirschman | A61B 17/7032 606/266 |
| 2007/0078460 A1* | 4/2007 | Frigg et al. | 606/61 |
| 2007/0118123 A1 | 5/2007 | Strausbaugh et al. | |
| 2007/0239159 A1 | 10/2007 | Altarac et al. | |
| 2007/0281274 A1 | 12/2007 | Schraffran et al. | |
| 2008/0009862 A1 | 1/2008 | Hoffman | |
| 2008/0147129 A1 | 6/2008 | Biedermann et al. | |
| 2009/0076552 A1 | 3/2009 | Tornier | |
| 2009/0198280 A1 | 8/2009 | Spratt et al. | |
| 2009/0281550 A1* | 11/2009 | Keller | 606/99 |
| 2009/0306721 A1* | 12/2009 | Kirschman | 606/267 |
| 2010/0152785 A1 | 6/2010 | Forton et al. | |
| 2010/0212460 A1 | 8/2010 | Buss et al. | |
| 2010/0298891 A1 | 11/2010 | Jackson | |
| 2010/0305621 A1 | 12/2010 | Wang et al. | |
| 2010/0312288 A1 | 12/2010 | Hammill, Sr. et al. | |
| 2011/0077694 A1 | 3/2011 | Biedermann et al. | |
| 2011/0152940 A1* | 6/2011 | Frigg et al. | 606/264 |
| 2011/0160778 A1 | 6/2011 | Elsbury | |
| 2011/0172714 A1 | 7/2011 | Boachie-Adjei et al. | |
| 2011/0178559 A1 | 7/2011 | Barry | |
| 2011/0263945 A1 | 10/2011 | Peterson et al. | |
| 2012/0031792 A1* | 2/2012 | Petit | 206/438 |
| 2012/0046699 A1 | 2/2012 | Jones et al. | |
| 2013/0096624 A1 | 4/2013 | Di Lauro et al. | |
| 2013/0110176 A1 | 5/2013 | Rezach et al. | |
| 2013/0226243 A1 | 8/2013 | Kraus | |

OTHER PUBLICATIONS

International Search Report and Written Opinion, PCT/US2014/061293, dated Jan. 23, 2015, 12 pages.

U.S. Office Action, U.S. Appl. No. 14/037,011, dated Jun. 5, 2015, 30 pages.

U.S. Office Action, U.S. Appl. No. 14/059,203, dated May 18, 2015, 46 pages.

U.S. Office Action, U.S. Appl. No. 14/092,154, dated Dec. 24, 2015, 11 pages.

* cited by examiner

BAYONET COUNTER-TORQUE WRENCH

TECHNICAL FIELD

Described herein is a bayonet counter-torque wrench having engaging slots conformed to fit over and lock a rod during spinal bone screw tightening such that the tool is maintained in an orientation perpendicular to the rod.

BACKGROUND

Counter-torque wrenches are used to help prevent undesired forces from being transmitted to spinal bone screws, thereby minimizing forces that may otherwise result in the screw breaking through bone as tightening torques are applied. Known counter-torque wrenches incorporate two straight slots configured to receive a rod and can pivot on the rod or be otherwise skewed relative to the rod when engaged with the rod. That is, the body of the wrench may not always be perpendicular to the axis of the rod. When a standard counter-torque wrench engages the rod and the screw body, there is no geometry for the wrench body to key into to promote a perpendicular orientation between the screw body and the rod. A standard counter-torque wrench can pivot on the rod or otherwise be skewed relative to the rod when it engages both the screw body and the rod. If the screw body is forced to stay in this skewed orientation, the set screw's ability to clamp the rod can be negatively impacted since it may not make flush contact with the rod.

Moreover, the use of known counter-torque wrenches permits screws to rotate out of alignment relative to the rod during tightening if the counter-torque wrenches are levered on during the act of tightening. Compressing across screws with a standard counter-torque wrench in place can cause the screw to translate as well as rotate out of proper alignment if force is not applied to the counter-torque wrench to reorient the screw into the proper orientation. The misaligned condition caused by levering on the standard counter-torque wrench may result in a gap between a set screw and the rod. The act of tightening the set screw would need to overcome any forces preventing proper orientation.

SUMMARY

It is desirable to have a counter-torque wrench that automatically maintains a perpendicular orientation between a longitudinal axis of the rod and a longitudinal axis of the torque wrench body. It is also desirable to have a counter-torque wrench that automatically maintains a co-linear orientation between a longitudinal axis of the screw body and the longitudinal axis of the torque wrench body during tightening of the set screw onto the rod.

According to one aspect of the invention, a counter-torque wrench may comprise a handle; a body having first and second ends, wherein the handle is attached to the first end of the body; and a rod engaging member attached to the second end of the body and comprising a bore sized to mate with a bone screw body; and first and second generally opposing slots, wherein each slot comprises: a pocket formed by a curved feature of each slot; and a prong extending into each slot, the prong creating a generally L-shaped slot; wherein the opposing slots are sized and shaped to at least partially receive and releasably attach to a spinal implant rod in an engaged position perpendicular to the body when the counter-torque wrench is rotated in a counter-clockwise direction.

In other embodiments, the counter-torque wrench may comprise a handle, and an elongated body comprising a bore therethrough, the body having first and second ends, wherein the handle is attached to the first end of the body. Additionally, in such embodiments, the counter-torque wrench may comprise a rod engaging member attached to the second end of the body and comprising a bore corresponding to the bore through the elongated body and sized to mate with a bone screw body. The rod engaging member may further comprise first and second opposing slots, wherein each slot comprises a linear wall opposing a nonlinear wall having a pocket formed by at least one curved feature, and wherein the pocket is sized and shaped to releasably attach to a spinal implant rod.

In some embodiments of the invention, the rod engaging member is sized and oriented to provide substantial perpendicular alignment between a longitudinal axis of a rod engaged in the pockets and a longitudinal axis of the counter-torque wrench body.

In certain embodiments of the invention, the rod engaging member is sized and oriented to provide substantial co-linear alignment between a longitudinal axis of the bone screw body and a longitudinal axis of the counter-torque wrench body.

In some embodiments of the invention, the rod engaging member is integrally formed with the counter-torque wrench body. In other embodiments of the invention, the rod engaging member is removably attached to the counter-torque wrench body.

In some embodiments of the invention, the handle is integrally formed with the counter-torque wrench body. In other embodiments of the invention, the handle is removably attached to the counter-torque wrench body.

DETAILED DESCRIPTION

Figures 1A, 1B:
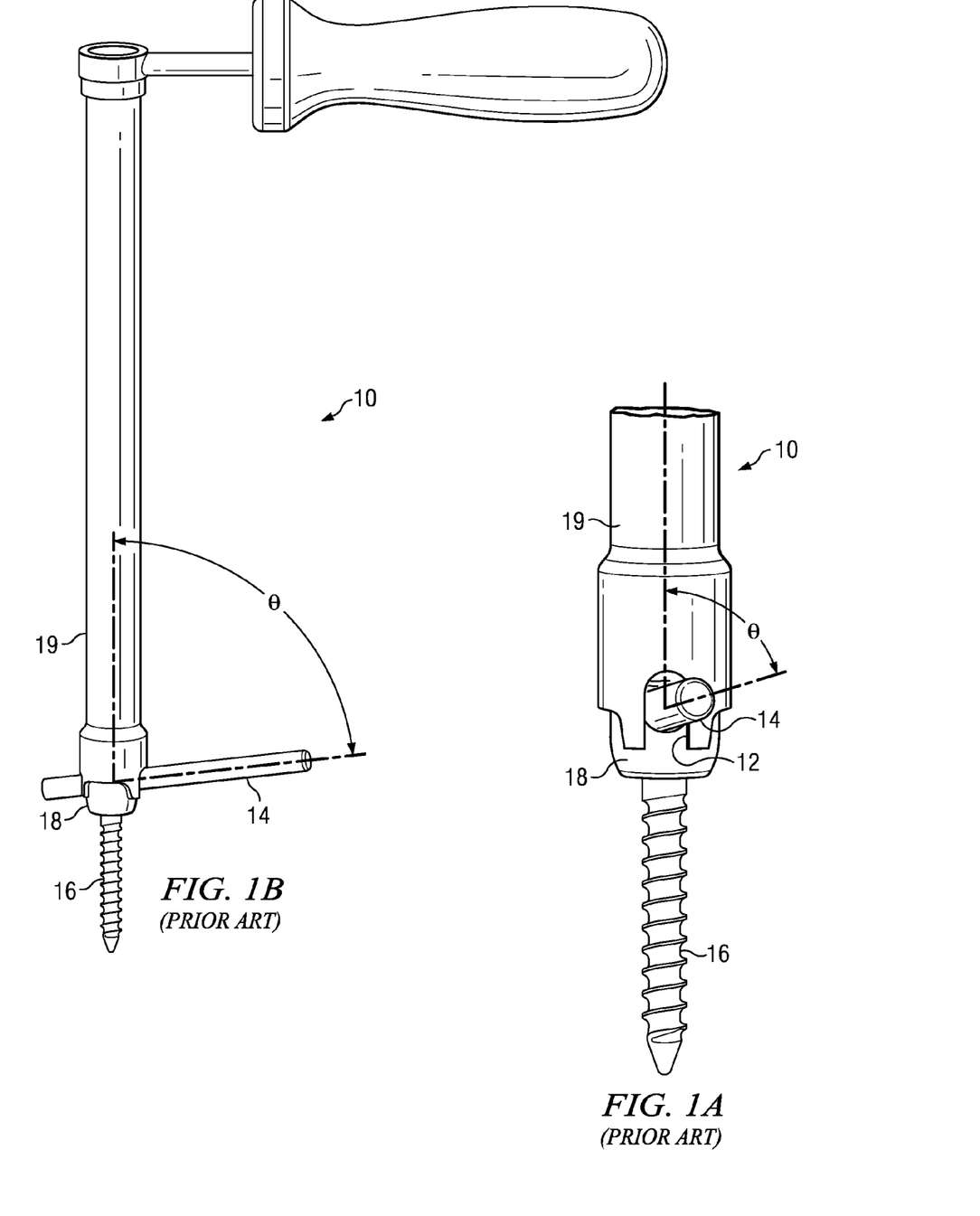
FIG. 1A illustrates a perspective view of a prior art counter-torque wrench showing a skewed orientation between the longitudinal axis of the rod and the longitudinal axis of the body of the wrench.
FIG. 1B illustrates a second perspective view of a prior art counter-torque wrench showing the skewed orientation between the longitudinal axis of the rod and the longitudinal axis of the body of the wrench.

Counter-torque wrenches are currently used to help prevent undesired forces from being transmitted to spinal bone screws, thereby minimizing the forces that may otherwise result in the screw breaking through bone as tightening torques are applied. However, the counter-torque wrenches known in the art, as shown in FIGS. 1A and 1B, can pivot on a rod or otherwise be skewed relative to the rod. As shown in FIGS. 1A and 1B, the known counter-torque wrench 10 includes a wrench body 19 that incorporates two straight slots 12. The wrench body 19 is operable to be configured with a mating bore that may receive a bone screw assembly, comprised of both a bone screw 16 and a bone screw body 18, and may also receive a rod 14. When the wrench body 19 is placed over the bone screw 16 and the bone screw body 18, the known counter-torque wrench 10 can pivot on the rod 14 or be otherwise skewed relative to the rod 14 when engaged with the rod 14. That is, the longitudinal axis of the wrench body 19 is not always perpendicular to the longitudinal axis of the rod 14 and can be less than 90 degrees, as illustrated by θ in FIGS. 1A and 1B.

In such a skewed orientation, the ability of a set screw (internal, not shown) to efficiently clamp the rod 14 is negatively impacted as the set screw and the bone screw assembly may not make flush contact with the rod 14. Moreover, use of the known counter-torque wrench 10 permits the bone screw 16 to rotate out of alignment relative to the rod 14 during tightening if the known counter-torque wrench 10 is levered on during the act of tightening. Specifically, the known counter-torque wrench 10 permits the existence of both a gap between the bone screw assembly and the rod 14 and a gap between the rod 14 and the slots 12 and the set screw.

Figure 2A:
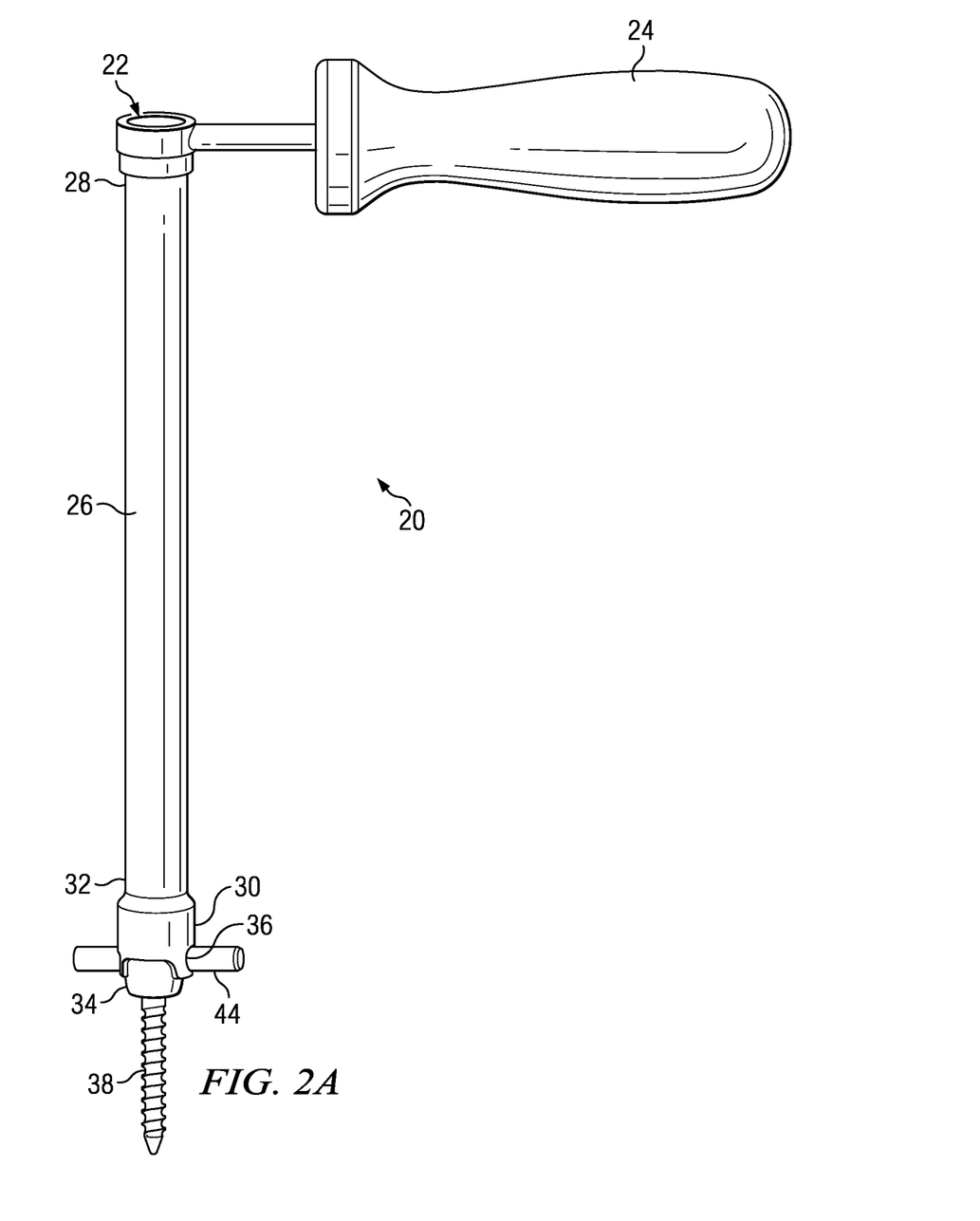
FIG. 2A illustrates a side elevation view of an embodiment of the inventive counter-torque wrench in position over a rod engaged in the head of a screw, in accordance with the present invention.

Referring now to FIG. 2A, one embodiment of the inventive counter-torque wrench 20 may include a handle 24 which engages a first end 28 of a wrench body 26. As shown in FIG. 2A, the longitudinal axis of the handle 24 may be placed perpendicular to the longitudinal axis of the wrench body 26. However, in alternative embodiments of the inventive counter-torque wrench 20, the longitudinal axis of the handle 24 may alternatively be aligned with the longitudinal axis of the wrench body 26. Moreover, in other embodiments, the longitudinal axis of the handle 24 may alternatively be oriented at an angle greater than or less than 90 degrees, with respect to the longitudinal axis of the wrench body 26. The handle 24 may be integral with or removable from the wrench body 26 in alternative embodiments of the invention. Moreover, the handle 24 may even be rotatable around the longitudinal axis of the wrench body 26.

In an embodiment, the wrench body 26 may preferably be tubular. "Tubular," as used herein, means having an inner bore and a wall and having any geometric cross section, including circular, square, hexagonal and the like. A tubular wrench body 26 may further permit a surgeon to insert a set screw (not shown) and a driver/holder (not shown) through the counter-torque wrench body 26 at an opening 22 if desired. Additionally, the tubular shaped body 26 may also enable tools to pass through the wrench body 26 at opening 22 to tighten the set screw, thereby clamping on a rod 44.

Also shown in FIG. 2A is a rod engaging member 30 disposed on a second end 32 of the wrench body 26. The rod engaging member 30 may be tubular in shape having an internal bore (not shown), as discussed in more detail in FIG. 6. The rod engaging member 30 may be further configured to fit over a bone screw body 34 of a bone screw assembly, as discussed in more detail in FIG. 2B.

Referring back to FIG. 2A, the rod engaging member 30 may further include two slots 36 within the tubular wall of the rod engaging member 30 and spaced opposing each other. The two slots 36, as described in more detail below in FIG. 3, may advantageously promote a perpendicular orientation between the body of the bone screw body 34 and the rod 44 by incorporating two "L"-shaped slots 36 that are perpendicular to the internal bore (not shown) of the rod engaging member 30. By incorporating "L"-shaped slots 36, forces may be applied to both the wrench body 26 and the rod 44, thereby promoting perpendicular orientation between the wrench body 26 and the rod 44 when the partial moon cut-out of the "L"-shaped slots 36 engage the rod 44. While the "L"-shaped slots 36 engage the rod 44, the inner bore (not shown) of the rod engaging member 30 may engage the outside surface of the bone screw body 34, thereby promoting perpendicular alignment between the bone screw body 34 and the rod 44.

Figure 2B:
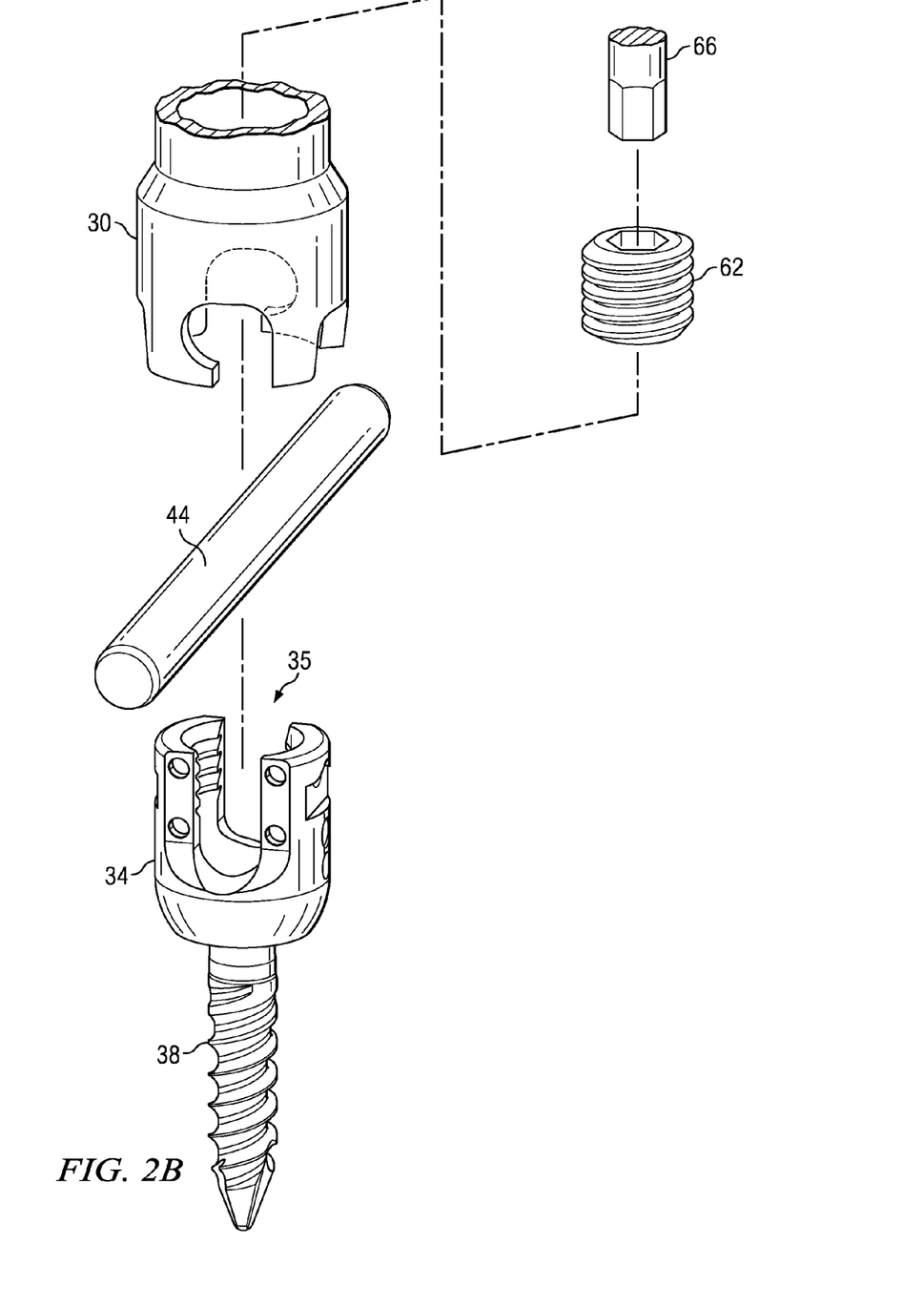
FIG. 2B illustrates an exploded view of an embodiment of the inventive counter-torque wrench in position over a rod engaged in the head of a screw, in accordance with the present invention.

Referring now to FIG. 2B, an exploded view of an embodiment of the inventive counter-torque wrench 20 of FIG. 2A is shown, in accordance with the present disclosure. As described in more detail in FIG. 6, a bone screw assembly 35 may comprise both the bone screw body 34 and the bone screw 38 and may be configured to receive the rod 44. The bone screw body 34 and the bone screw 38 of the bone screw assembly 35 may be manufactured as a single component with a static co-axial orientation between the bone screw body 34 and the bone screw 38. Conversely, in a separate embodiment, the bone screw body 34 and the bone screw 38 of the bone screw assembly 35 may be manufactured from separate components to allow the bone screw 38 to pivotably rotate away from a co-axial alignment with the longitudinal axis of the bone screw body 34 in order to allow the orientation of the longitudinal axis of the bone screw 38 to differ from that of the bone screw body 34.

The rod engaging member 30 may be configured to be received over the rod 44 and the bone screw assembly 35 and may be rotated counterclockwise to "lock" the rod 44 into the slots in the rod engaging member 30. Once engaged, a set screw 62 may be driven through the opening of the wrench body (not shown) and an inner bore of the rod engaging member. As described in more detail in FIG. 6, the set screw 62 may be engaged with internal threads in the bone screw body 34, and when the set screw 62 is tightened, the set screw 62 may clamp the rod 44 to the bone screw body 34.

Figure 3:
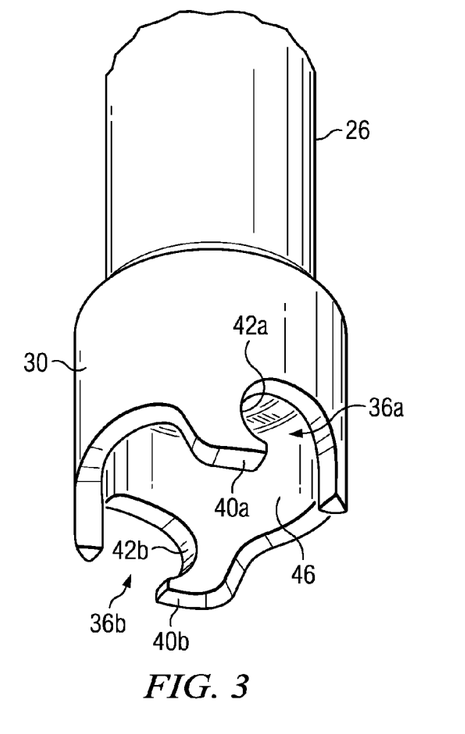
FIG. 3 illustrates a perspective view of an embodiment of the rod engaging member in accordance with the disclosed principles, in accordance with the present invention.

Referring now to FIG. 3, a detailed perspective view of the rod engaging member 30 is shown. As discussed in FIG. 2A, the rod engaging member 30 may include an internal bore 46. The tubular walls defining the inner bore 46 may be perpendicular to the opposing "L"-shaped slots 36 so as to promote the desired perpendicular orientation between the bone screw body (not shown, reference 34 in FIG. 2A) and the rod (not shown, reference 44 in FIG. 2A) when the rod is received into the rod engaging member 30.

Referring again to FIG. 3, the "L"-shaped slots 36a and 36b are shown as generally oval in shape defining an opening through which the rod (not shown) may pass in use. On a first end of each slot 36 (36a and 36b) is a curved prong 40 (40a and 40b) forming a pocket 42 (42a and 42b) in which a rod (not shown) may be removably "locked" into position. Each curved prong 40 defines an "L"-shaped slot 36, although in other embodiments, the opposing slots 36 could alternatively be described as being "C"-shaped or crescent-shaped, among other shapes. Each "L"-shaped slot 36 extends substantially vertically from the opening defining the inner bore 46 of the rod engaging member 30 and each prong 40 defines the pocket 42 in slot 36. The exact shape and size of the curved prongs 40a and 40b may vary in various embodiments of the inventive counter-torque wrench provided that each curved prong 40a and 40b forms the pockets 42a and 42b such that a rod (not shown) may be at least partially held within the pockets 42a and 42b in an engaged position when the counter-torque wrench 30 is rotated in a counter-clockwise direction, as discussed in more detail in FIG. 4. According to one embodiment, the L-shaped slots 36 include a curved feature that substantially matches a circumferential curvature of the spinal implant rod.

As can be further seen in FIG. 3, the curved prong 40*a* of the first slot 36*a* may be located opposite the curved prong 40*b* of the second slot 36*b*. That is, the prongs 40*a* and 40*b* are not adjacent to each other. This alternate placement of the prongs 40*a* and 40*b* allows the rod engaging member 30 to be placed over a rod (not shown) and "locked" into place by engaging opposing sides of a rod (not shown) in opposite pockets 42*a* and 42*b* of the rod engaging member 30. When the rod 44 is properly engaged and "locked" into place, the rod 44 may be perpendicularly orientated to the wrench body 26 and the bone screw body (not shown).

Figure 4:
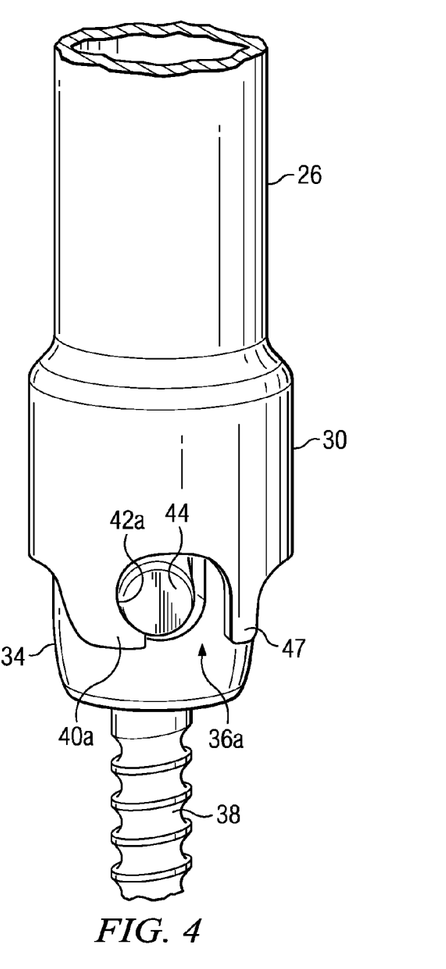
FIG. 4 illustrates a perspective view of another embodiment of the rod engaging member having a single pocket in each slot, in accordance with the present invention.

Referring now to FIG. 4, once the rod engaging member 30 receives the rod 44 through the "L"-shaped slots 36, proper engagement between the rod engaging member 30 and the rod 44 is attained by rotating the counter-torque wrench body 26 counter-clockwise. The counter-clockwise rotation of the counter-torque wrench engages the rod engaging member 30 with the rod 44 such that the first "L"-shaped slot 36*a* contacts the rod 44 at pocket 42*a*. While not shown in the perspective of FIG. 4, the second "L"-shaped slot 36*b* likewise contacts the rod 44 at pocket 42*b* when the rod engaging member 30 is engaged with the rod 44.

Once the rod 44 is "locked" into opposing pockets 42*a* and 42*b*, the longitudinal axis of the wrench body 26 of the inventive counter-torque wrench 20 may be held perpendicular to the longitudinal axis of the rod 44, as shown in FIG. 2A. The perpendicular orientation between the wrench body 26 and the rod 44 may advantageously align the rod 44 perpendicular to the bone screw body 34 inside the rod engaging member 30 so that the set screw (not shown) can make flush contact with the rod 44, as described in more detail in FIG. 6. Referring again to FIG. 4, each "L"-shaped slot 36 may optionally include a straight prong 47 opposite and adjacent to the corresponding curved prong 40 defining the slot 36.

Figure 5:
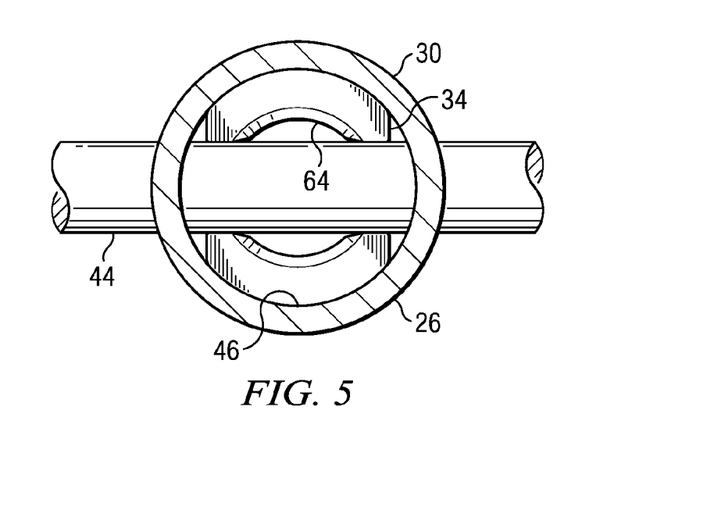
FIG. 5 illustrates a top view of the rod engaging member and screw body, in accordance with the present invention.

Referring now to a top view of the rod engaging member 30 as shown in FIG. 5, as the slots (not shown) in the rod engaging member 30 engage with the rod 44, the internal bore 46 of the wrench body 26 may engage with the bone screw body 34 of the bone screw assembly. FIG. 5 further illustrates that internal threads 64 that may be configured to mate with a set screw (not show) received through the internal bore 46. In operation, as the rod 44 is engaged in the "L"-shaped slots 36, as described in FIGS. 3-4, the internal bore 46 in the wrench body 26 engages with an outside diameter of the bone screw body 34, thereby promoting a co-axial alignment between the wrench body 26 and the bone screw body 34 and a perpendicular orientation between the longitudinal axis of the rod 44 and the longitudinal axis of the bone screw body 34.

Figure 6:
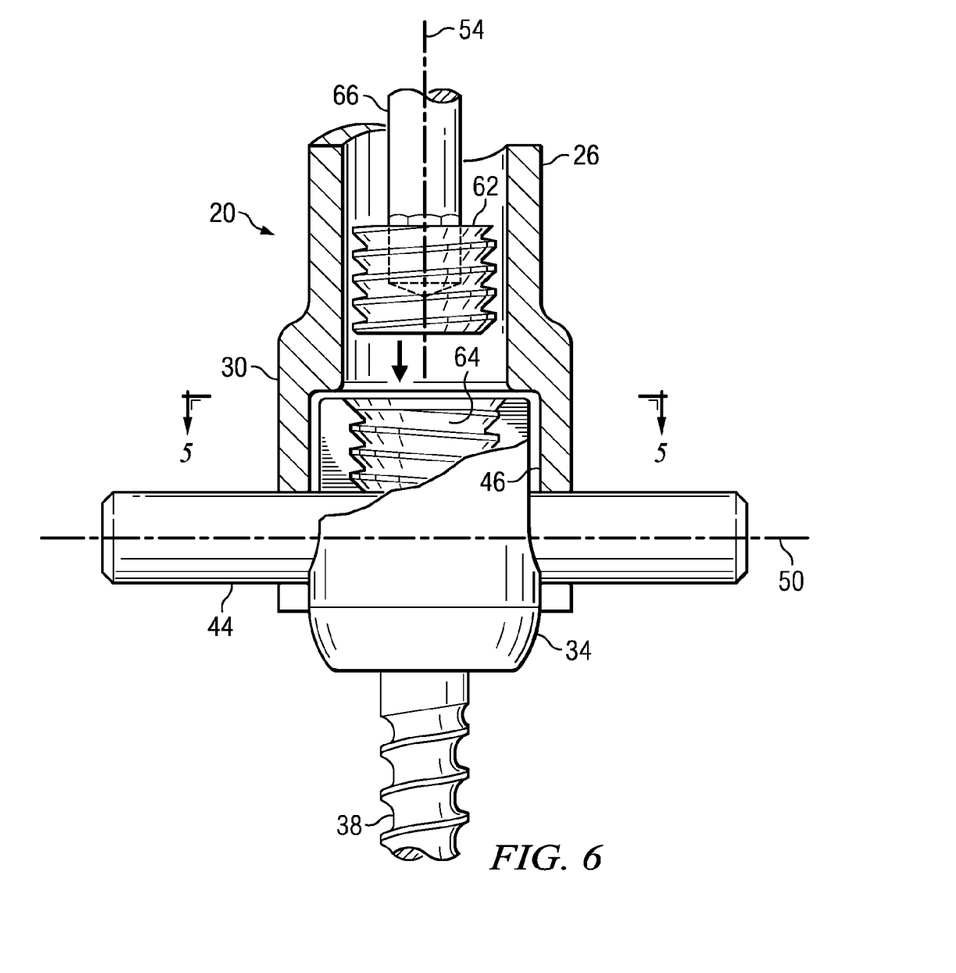
FIG. 6 illustrates a side elevation view of the rod engaging member of the counter-torque wrench in position over the rod engaged with the screw, in accordance with the present invention.

Referring now to FIG. 6, when the counter-torque wrench 20 is placed over the rod 44 and the bone screw body 34, the set screw 62 may be configured to engage with the threads 64 located within the bone screw body 34 in order to clamp the rod 44 perpendicular to the bone screw body 34. The threads 64 shown in FIG. 6 are located within an internal wall of the bone screw body 34 such that applying a clockwise torque to the set screw 62 will rotate the set screw 62 downwards against the rod 44. The set screw 62 may be engaged with the threads 64 in the bone screw body 34 prior to the counter-torque wrench 20 being engaged with the rod 44, or the set screw 62 may be inserted through the opening 22 and through the inner bore 46 of the counter-torque wrench 20, as shown in FIG. 2. If the set screw 62 is inserted through the opening 22, the set screw 62 may be passed through the inner bore 46 of the wrench body 26 with the aid of the set screw driver/holder 66.

When the counter-torque wrench 20 receives the bone screw body 34 of the bone screw assembly into the internal bore 46 of the wrench body 26 and the rod 44 is "locked" into the rod engaging member 30, as discussed in FIGS. 3 and 4, both the bone screw body 34 and the rod 44 may be engaged in order to promote a co-axial orientation between the bone screw body 34 and the wrench body 26 and a perpendicular orientation between a longitudinal axis 54 of the wrench body 26 and a longitudinal axis 50 of the rod 44. In order to "lock" the rod 44 into place, the surgeon may first apply counter-torque forces by hand to the counter-torque wrench 20 in a counter-clockwise rotation in order to engage the rod 44 into the slots 36. Simultaneously, the surgeon may apply torque to the set screw 62, referring back to FIG. 6, with the set screw driver/holder 66 in a clockwise rotation through the internal bore 46 of the wrench body 26 in order to tighten the set screw 62. When the set screw 62 is tightened, the set screw 62 may clamp the rod 44 to the bone screw body 34, thereby promoting a perpendicular orientation between the two. As previously discussed, the rod engaging member 30 and the bone screw body 34 may be sized and oriented to provide a substantially co-linear alignment between the longitudinal axis 54 of the wrench body 26 and the longitudinal axis of the bone screw body 34.

In one embodiment, the design the bone screw assembly, as shown in FIG. 2B, may allow the bone screw 38 to pivot independently of the bone screw body 34, thereby allowing a surgeon to pivot the bone screw 38 into proper alignment without changing the orientation of the bone screw body 34 engaged within the internal bore 46 of the counter-torque wrench 20. This functionality may allow the surgeon to insert adjacent bone screw assemblies 35 at different orientations in adjacent vertebrae and then connect the bone screw assemblies 35 with the rod 44 via the substantially aligned bone screw bodies 34 such that the rod 44 may be perpendicular to each bone screw body 34 may be connected between the bone screw assemblies 35. By maintaining the perpendicular orientation between each bone screw body 34 and rod 44, each set screw 62 may be configured to properly clamp with the connecting rod 44 even if each of the bone screws 38 are inserted into bone at different orientations.

Proper use of the counter-torque wrench 20, as shown in FIGS. 2A-6, may consist of inserting the tool 66 and the set screw 62 through the opening 22 and internal bore 46 of the wrench body 26 onto the rod 44 and the bone screw body 34 to clamp the rod 44 to the bone screw body 34, as shown in the exploded view of FIG. 2B. Referring back to FIGS. 2A-6, prior to tightening the set screw 62 in the internal threads 46, the counter-torque wrench 20 may be configured to be rotated counter-clockwise such that the rod 44 is properly engaged and "locked" into the pockets 42 formed by the prongs 40 defining the "L"-shaped slots 36 on the rod engaging member 30. When the rod 44 may be properly engaged and "locked" into the rod engaging member 30, and prior to semi-tightening ("semi-snugging") the set screw 62 and final tightening of the bone screw 38, the "L"-shaped slots 36 may aid in aligning the rod 44 in a perpendicular orientation to the bone screw body 34 such that the set screw 62 may make flush contact with the rod 44.

When properly engaged, the rod 44 is perpendicular to the wrench body 26 and the bone screw body 34 and may prevent inadvertent levering or misalignment of the counter-torque wrench 20 components during final tightening. Once the rod 44 is properly engaged, the set screw 62 may be tightened more smoothly against the rod 44 by rotating the set screw 62 in a clockwise rotation with the driving tool 66 in order to mate the set screw 62 with the internal threads 64 of the bone screw body 34. Tightening the set screw 62 clamps the perpendicularly aligned rod 44 against the bone screw body 34. When properly oriented perpendicular to the rod 44, the bone screw body 34 may be less prone to squeaking and galling.

As shown in FIGS. 2A-6, the rod engaging member 30 is generally tubular in shape and has a diameter slightly larger than that of the wrench body 26. It will be understood that in alternative embodiments, the diameter of the rod engaging member 30 may be equal to or less than the diameter or cross sectional length of the wrench body 26. In alternative embodiments of the inventive counter-torque wrench, the rod engaging member 30 may be integrally formed with the wrench body 26 or may be removably attached to the wrench body 26.

Additionally, as shown in FIGS. 2A-6, the rod engaging member 30 is generally shown to include cutouts between the prongs 40 and 47 which may exist so that rod engaging member 30 can mate with alternative body styles of the bone screw assembly. It will be understood that in alternative embodiments, the cutouts may not be needed and that the only openings in the rod engaging member 30 may be the slots 36 for receiving the rod 44.

While various embodiments have been described above, it should be understood that they have been presented by way of example only, and not limitation. Thus, the breadth and scope of a preferred embodiment should not be limited by any of the above described exemplary embodiments, but should be defined only in accordance with the claims and their equivalents for any patent that issues claim1ng priority from the present provisional patent application.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Brief Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:
1. A spinal implantation system, comprising:
a bone screw assembly comprising a U-shaped bone screw body and a bone screw;
a spinal implant rod operable to be received within the U-shaped bone screw body; and
a counter-torque wrench comprising:
a handle;
a body comprising a proximal end and a distal end and an opening extending therebetween, the body further comprising a length defined as the distance from the proximal end to the distal end, wherein the handle is attached to the proximal end of the body; and
a rod engaging member attached to the distal end of the body, the rod engaging member comprising:
a bore sized to receive the U-shaped bone screw body of the bone screw assembly; and
first and second opposing slots formed entirely within the distal end of the body and which traverse less than half of the length of the body, wherein each slot comprises:
a prong extending into each slot, the prong creating a generally L-shaped slot; and
a pocket formed by a curved feature of each slot;
wherein the opposing slots are sized and shaped to releasably attach to the spinal implant rod in an engaged position perpendicular to the body of the counter-torque wrench when the counter-torque wrench is rotated in a counter-clockwise direction; and
wherein the body of the counter-torque wrench is operable to:
receive the U-shaped bone screw body of the bone screw assembly within the bore;
receive the spinal implant rod received within the U-shaped bone screw body within the bore of the rod engaging member; and
receive a set screw and a driver in the proximal opening of the body of the counter-torque wrench; and
align the bone screw assembly and the spinal implant rod with the driver;
such that the system perpendicularly aligns the U-shaped bone screw body of the bone screw assembly with the spinal implant rod when the spinal implant rod is locked in each formed pocket while the formed opposing slots are releasably attached to the rod in the engaged position.
2. The counter-torque wrench of claim 1, wherein the rod engaging member is integrally formed with the body.
3. The counter-torque wrench of claim 1, wherein the handle is integrally formed with the body.
4. The counter-torque wrench of claim 1, wherein the handle is removably attached to the body.
5. The counter-torque wrench of claim 1, wherein the handle is rotatable about a longitudinal axis of the body.
6. The counter-torque wrench of claim 1, wherein the at least one curved feature has a curvature substantially matching a circumferential curvature of the spinal implant rod.

* * * * *